United States Patent [19]

Waltonen et al.

[11] Patent Number: 5,230,921
[45] Date of Patent: Jul. 27, 1993

[54] FLEXIBLE PIEZO-ELECTRIC MEMBRANE

[75] Inventors: James R. Waltonen, Milwaukie; Ronald W. Schutz, Lake Oswego, both of Oreg.

[73] Assignee: Blacktoe Medical, Inc., Portland, Oreg.

[21] Appl. No.: 924,833

[22] Filed: Aug. 4, 1992

[51] Int. Cl.$^5$ .............................................. B05D 5/12
[52] U.S. Cl. ..................................... 427/100; 427/322; 367/180
[58] Field of Search ................ 427/100, 322; 367/180

[56] References Cited

U.S. PATENT DOCUMENTS

| 4,180,602 | 12/1979 | Schiavone | 427/100 |
| 4,375,818 | 3/1983 | Suwaki et al. | 128/662.06 |
| 4,391,282 | 7/1983 | Ando et al. | 128/662.06 |
| 4,415,679 | 11/1983 | Grot | 521/31 |
| 4,433,082 | 2/1984 | Grot | 524/755 |
| 4,437,032 | 3/1984 | Gelhard | 310/324 |
| 4,437,951 | 3/1984 | Bissot et al. | 204/98 |
| 4,453,991 | 6/1984 | Grot | 427/140 |
| 4,469,744 | 9/1984 | Grot et al. | 428/248 |
| 4,518,650 | 5/1985 | Grot et al. | 428/286 |
| 4,521,322 | 6/1985 | Broussoux et al. | 252/62.9 |
| 4,558,249 | 12/1985 | Lerch et al. | 310/324 |
| 4,631,436 | 12/1986 | Edinger | 310/332 |
| 4,671,292 | 6/1987 | Matzuk | 128/660.09 |
| 4,712,036 | 12/1987 | Gurich | 310/333 |
| 4,722,348 | 2/1988 | Ligtenberg et al. | 128/675 |
| 4,744,368 | 5/1988 | Young et al. | 128/662.04 |
| 4,787,394 | 11/1988 | Ogura | 128/660.03 |
| 4,802,458 | 2/1989 | Finsterwald et al. | 128/661.08 |
| 4,823,773 | 4/1989 | Naser et al. | 128/24 EL |
| 4,834,102 | 5/1989 | Schwarzchild et al. | 128/662.06 |
| 4,838,634 | 6/1989 | Bennion et al. | 427/322 |
| 4,855,163 | 8/1989 | Joffee et al. | 427/322 |
| 4,877,988 | 10/1989 | McGinniss et al. | 310/306 |
| 4,914,959 | 4/1990 | Mylvaganam et al. | 73/861.28 |
| 4,972,839 | 11/1990 | Angelsen | 128/662.06 |
| 5,035,247 | 7/1991 | Heimann | 128/715 |

FOREIGN PATENT DOCUMENTS 2546703 11/1984 France .

Primary Examiner—Michael Lusigan
Assistant Examiner—David M. Maiorana
Attorney, Agent, or Firm—Kolisch, Hartwell, Dickinson, McCormack & Heuser

[57] ABSTRACT

A piezo-electric flexible membrane is formed by treating a perfluorinated membrane in order to produce a membrane having an electrical resistance greater than $1 \times 10^9$ ohms. The resultant piezo-electric membrane may be used as an ultrasound transducer.

14 Claims, 2 Drawing Sheets

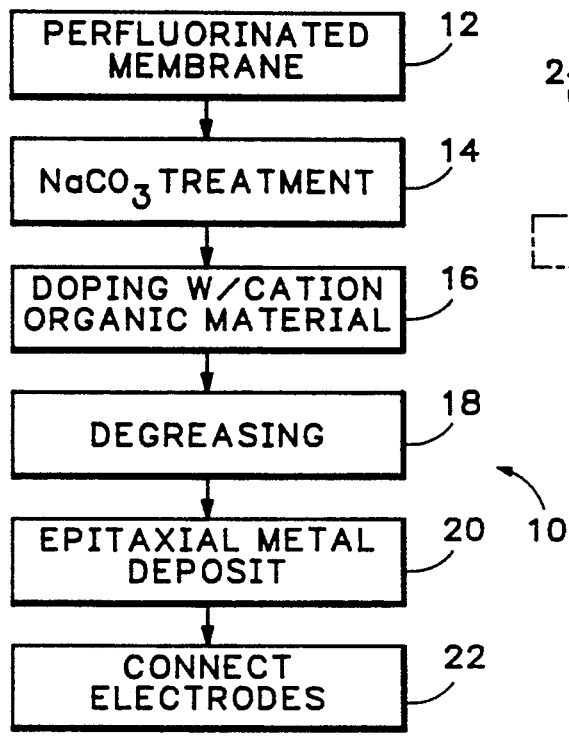
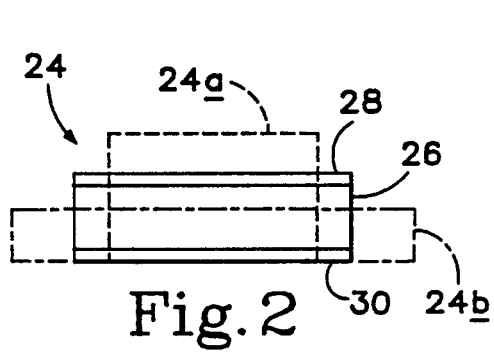
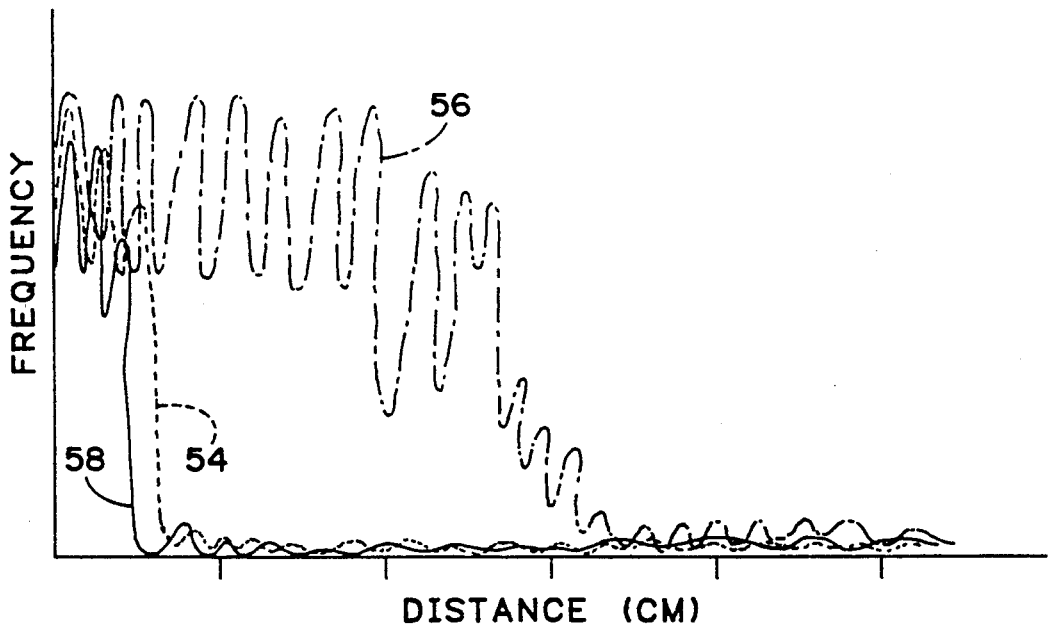

FLEXIBLE PIEZO-ELECTRIC MEMBRANE

BACKGROUND OF THE INVENTION

The invention relates to a flexible piezo-electric membrane, and specifically to a membrane which is suitable for use in an ultrasound transducer.

Known piezo-electric membranes operate under very tight voltage and frequency constraints. Additionally, such membranes exhibit piezo-electric effects by curling or twisting. Such effects limit the use of such membranes as ultrasonic transducers.

A number of forms of ultrasound transducer are known. The vast majority of ultrasound transducers incorporate some form of ceramic or metallic element which may have piezo-electric characteristics. In other instances, laminated membranes are disclosed which exhibit piezo-electric characteristics. The aforementioned devices, while suitable for their intended purposes, suffer a limitation in that the piezo-electric device is of relatively thick cross-section and therefore requires some form of carrier for supporting and activation of the piezo-electric device.

SUMMARY OF THE INVENTION

It is an object of the instant invention to provide a piezo-electric membrane which produces a "broad-side" response and which is suitable for use as an ultrasound transducer.

Another object of the invention is to provide an ultrasound transducer which is suitable for mounting on a carrier, such as a surgical glove, which will allow a physician to have a tactile sense of the body part being examined as well as to examine the body part ultrasonically.

A further object of the invention is to provide an ultrasound transducer incorporating a piezo-electric membrane which is responsive in conventional ultrasound frequencies and is therefore usable with existing ultrasound equipment.

Yet another object of the invention is to provide an ultrasound transducer which will generate signals appropriate to making ultrasound readings within a few millimeters of the ultrasound transducer.

A further object of the invention is to provide a piezo-electric membrane which is easily and inexpensively manufactured.

The piezo-electric flexible membrane of the invention is formed by treating a membrane, such as a perfluorinated membrane, in order to produce a membrane having an electrical resistance greater than $1 \times 10^9$ ohms. The resultant piezo-electric membrane may be used in an ultrasound transducer.

These and other objects and advantages of the invention will become more fully appreciated as the description which follows is read in conjunction with the drawings.

BRIEF DESCRIPTION OF THE DRAWINGS

FIG. 1 is a block diagram depicting the steps in making the flexible piezo-electric membrane of the invention.

FIG. 2 is a somewhat schematic depiction of what is referred to herein as "broad-side" response of a piezo-electric membrane.

FIG. 5 is a comparison trace of an ultrasound reading made with the piezo-electric flexible transducer of the invention and a conventional transducer.

DETAILED DESCRIPTION OF THE PREFERRED EMBODIMENT

Figure 3:
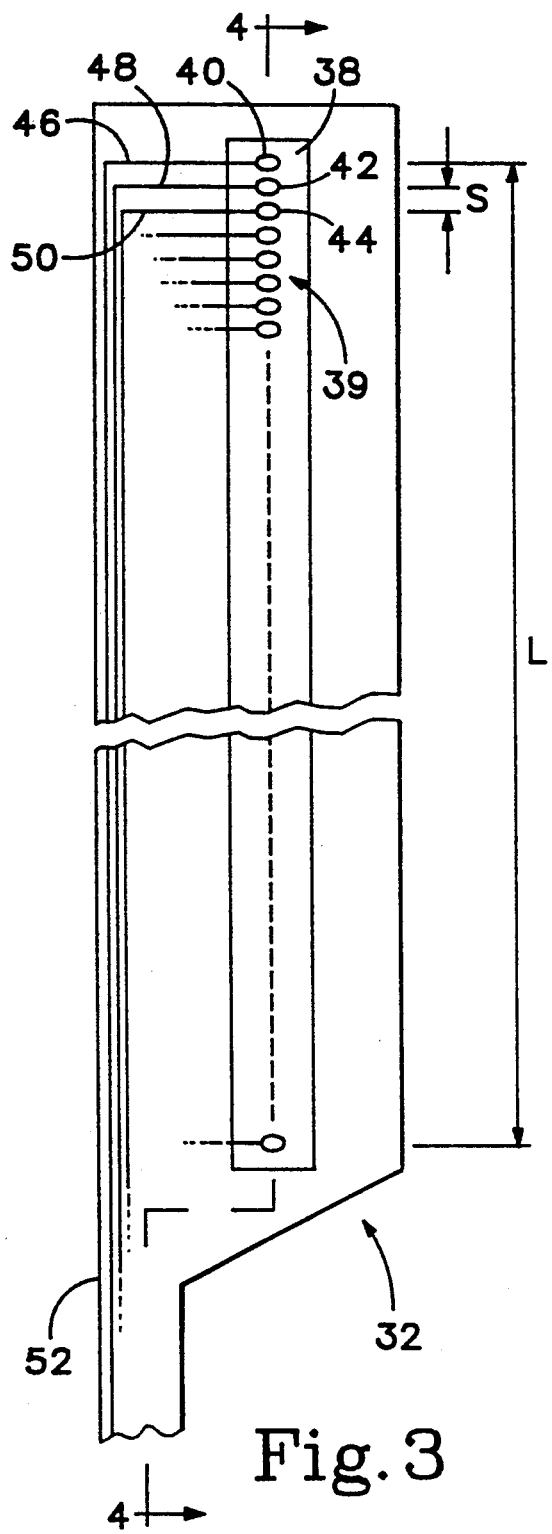
FIG. 3 is a top plan view of a piezo-electric array on a flexible membrane configured for use as an ultrasound transducer.

The piezo-electric flexible membrane of the invention is formed, in the preferred embodiment, from a perfluorinated membrane, which includes a carbonfluorine backbone chain having perfluoro side chains which contain sulfonic or carboxylic groups, and which may be represented as follows:

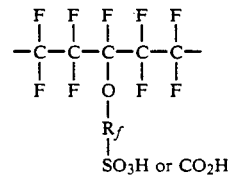

Such a membrane is manufactured and marketed by the Dupont Company under the name NAFION ® mark. NAFION ® membranes were first developed in 1962 and have been used primarily as a separator in electrolytic cells. The NAFION ® membranes, as manufactured, have a resistance on the order of $2.3-3.1 \times 10^6$ ohms, which is far too low to demonstrate any piezo-electric characteristics. While the NAFION ® membrane is quite suitable for its intended purpose, it does not exhibit piezo-electric characteristics until it is chemically treated, which effectively results in its being "poisoned", and rendered unsuitable for its intended purpose.

The method of making the ultrasound transducer of the invention is depicted in FIG. 1, generally at 10. As illustrated in FIG. 1, a perfluorinated membrane, which is a NAFION ® membrane in the preferred embodiment, block 12, is provided. The membrane has a nominal thickness of $1.5 \times 10^{-2}$ cm.

The membrane is treated with a hydrogen ion scavenger, such as sodium bicarbonate (NaCO3), for approximately one minute, block 14. Other compounds, such as NaOH, neutral pH buffers or complex polyphosphates, such as potassium phosphate monobasic, and CaCO3, have also been found to perform well in this step. The scavenger ties up free hydrogen ions in the membrane, initially raising the electrical resistance of the membrane. The following table sets forth the resistive properties of the membrane following treatment with various compounds:

TABLE 1

| Compound | Linear Resistance Ω/inch | Through Resistance Ω/cm² |
|---|---|---|
| untreated | $3.1 \times 10^6$ | $2 \times 10^6$ |
| water | $96 \times 10^6$ | $20 \times 10^6$ |
| NaCO3 | $1.0 \times 10^9$ | $80 \times 10^6$ |
| K2HPO3 | $69 \times 10^6$ | $40 \times 10^6$ |
| CaCO3 | $350 \times 10^6$ | $51 \times 10^6$ |

The membrane is subsequently treated with a cation-donating substance, such as an organic dye. In the preferred method of practicing the invention, yellow #5 dye is used, although methyl blue #1, red #40 and green are also suitable. This phase of the treatment takes approximately twenty-five minutes, block 16. The result setforth in the following table indicate the increase in resistivity from treatment only with the dyestuff for one minute:

TABLE 2

| Compound | Linear Resistance Ω/inch | Through Resistance Ω/cm$^2$ |
| --- | --- | --- |
| Blue #1 | $30 \times 10^6$ | $50 \times 10^6$ |
| Red #40 | $17 \times 10^6$ | $60 \times 10^6$ |
| Green | $24 \times 10^6$ | $74 \times 10^6$ |
| Yellow #5 | $33 \times 10^6$ | $75 \times 10^6$ |

Although the treatment with only one of the compound types increases the resistivity, it has been found that a combined treatment is more effective than even a single, longer duration treatment, as set forth in the following table:

TABLE 3

| Compound | Linear Resistance Ω/inch | Through Resistance Ω/cm$^2$ |
| --- | --- | --- |
| NacO$_3$ (1 min) followed by Yellow #5 (25 min) | $2.3 \times 10^9$ | $150 \times 10^6$ |
| Yellow #5 (25 min) | $51 \times 10^6$ | $100 \times 10^6$ |

After the above described treatments, the membrane is no longer suitable for its intended purpose as a separator, but does exhibit an increase in resistivity on the order of $1.5 \times 10^9$ ohms. The treated membrane, which now exhibits piezo-electric properties is degreased, block 18. It is then placed in an epitaxial vacuum chamber and is coated, at least on one side thereof, with a metal, block 20. In the preferred method, aluminum or gold is deposited on the membrane to a thickness of $5 \times 10^{-6}$ cm. Suitable masking may be provided to form a specific shape of the aluminum. After the metal is applied, the combined structure is a piezo-electric unit. Electrodes are then applied to the surface of the membrane, block 22.

When a current is applied to the membrane through the electrodes, the membrane exhibits what is referred to herein as "broad-side" piezo-electric characteristics. This is best illustrated in FIG. 2, wherein a piezo-electric unit 24, consisting of a membrane 26, and metal layers 28, 30, is depicted in cross-section in a relaxed state. When an electric current is passed through piezo-electric unit 24, it will either (1) contract, assuming the general shape depicted at 24a in dashed line, or (2) expand, as depicted by dash-dot line 24b. When used as a transducer, the membrane will alternately expand and contract, changing thickness, thereby producing sound waves of the desired frequency, and will produce an electrical current as the returned sound waves impinge on the membrane, causing it to expand and contract.

The membrane of the invention differs from known piezo-electric membranes which tend to curl when a current is applied thereto, and which respond to the receipt of vibrations by generating an electrical signal when the membranes are deformed in a circular or curl-like fashion.

The piezo-electric membrane of the invention has been demonstrated to be particularly effective using perfluorinated membranes because such membranes have high electrical stability. It is conceivable that other organic chains could be used so long as a polarizing radical is present at 90° to the chain.

Figure 4:
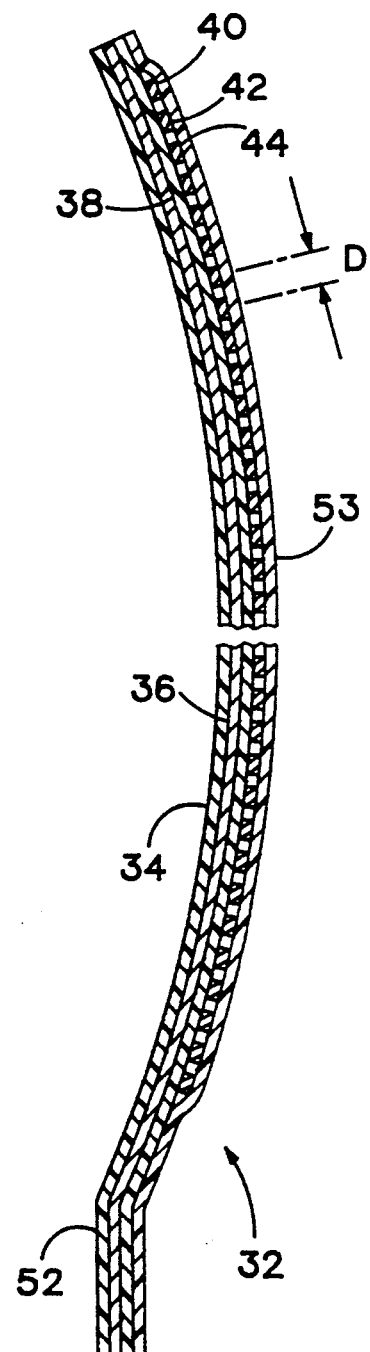
FIG. 4 is a medial side elevation of the transducer array taken generally along the line 4—4 of FIG. 3.

Turning now to FIGS. 3 and 4, a transducer using the piezo-electric membrane of the invention is depicted generally at 32. Transducer 32 has an operable length L which, in the preferred embodiment is approximately six centimeters in length, which is determined by the operational frequency, in this case, 3 MHz. Transducer 32 is of a size, therefore, which is suitable for incorporation onto or into a surgical glove, wherein the transducer may be manipulated by a physician's fingers in order to position the transducer units in their desired location.

In the preferred embodiment, transducer 32 includes a base layer 34 which may be formed of a polymer such as mylar, and which has a thickness of approximately $2.54 \times 10^{-3}$ centimeters. The next layer is a grounding material 36 which may be some form of thin conductive material, such as aluminum. This layer may take the form of an adhesive film, and have a thickness on the order of $7.62 \times 10^{-3}$ centimeters. The next layer is the piezo-electric membrane 38 which has been described previously herein. The membrane is formed with an array of metalized structures formed on one surface thereof. In the preferred embodiment, membrane 38 is equipped with a sixty-four unit array 39 of deposited metal, such as those depicted at 40, 42 and 44, which form individual transducers in the array. The metalized "buttons" or elements may be circular or oval in form, and the precise dimensions will depend on the frequency which is to be achieved by the transducer. Other forms or shapes may be used, depending on the frequency and desired dispersion angle(s). The metal elements are spaced apart a distance S from center to center, which in the preferred embodiment is approximately 6 millimeters. The oval metal elements which are depicted have a minor axis of approximately 2 millimeters and a major axis of approximately 25 millimeters.

Each metal element 40, 42, 44 has an electrical lead 46, 48, and 50, respectively, which extend the length of transducer 32 into a narrowed portion 52 thereof, which contains a suitable connector for connecting the transducer to a cable from a conventional ultrasound machine. As previously noted, the metal layers may be deposited upon a single piece of piezo-electric membrane through epitaxial deposition. Suitable masking will allow the formation of all of the metal elements in a single process.

The transducer is covered with another layer of mylar 53 which totally encapsulates the piezo-electric membrane, the metal elements thereon, and the leads running from the individual metal elements.

In the preferred embodiment, and now referring now to FIG. 4, transducer 32 is arranged with a curve such that a dispersion angle D is equal to approximately 1.5 degrees, which corresponds to the dispersion angle of the individual metal element transducers when constructed according to the parameters previously described herein and when the transducer is operated at a nominal frequency of approximately 3 MHz, which is a conventional frequency for ultrasound transducers. With such an arrangement, it may be seen that the area within the immediate vicinity of the transducer is fully subjected to ultrasound waves, and that any return waves will be detected by the individual metal element transducers within the array. The ultrasound unit which drives and interprets the transducer will be provided with suitable electronics to drive the transducer array and interpret the signals returning therefrom. As there are other arrayed ultrasound transducers commercially available, it is believed that the modifications to provide such electronics are within the knowledge of those ordinary skill in the art.

Turning now to FIG. 5, a graph is presented which includes three traces. The first trace, shown in dashed lines at 54, is representative of an A mode (amplitude verses time) ultrasound operation operating with only background noise (no transducer). The second dashed-dot trace 56 represents a return form a conventional ceramic transducer. It should be noted that when compared to the distance, or depth markings along the ordinate of the graph, the background noise produced by this type of transducer is sufficiently high to preclude meaningful readings within approximately three centimeters of the transducer.

The final, solid line trace 58 is representative of a return from a transducer constructed according to the invention. What is striking is, when compared to the ceramic transducer, that the piezo-electric membrane transducer of the invention will provide meaningful readings within approximately one-half centimeter of the transducer, unlike the ceramic transducer which requires a much greater depth. The field of view then of the transducer of the invention makes the transducer particularly well suited for use in procedures such as cardiac surgery, wherein the transducer may be used to determine the location of blockages within coronary arteries to enable a surgeon to determine where the blockage begins, which in turn enables a surgeon to determine where to place a graft in the case of a bypass surgery.

The piezo-electric membrane transducer of the invention responds at two to three volts, compared to the sixty to one hundred volts which is required for quartz and ceramic transducers. The transducer of the invention is operable at the higher voltages, but works well below such voltages, which are potentially at lethal shock levels.

Anther feature of the invention is that a transducer using the piezoelectric membrane does not require dampening to eliminate ringing because the transducer does not operate at a resonant frequency of the piezo-electric membrane. The transducer will image in the immediate near field, as compared to conventional transducers which require a significant ring-down time.

Although a preferred method of forming the piezo-electric membrane at a preferred embodiment of the transducer has been disclosed, it should be appreciated that variations and modifications may be made thereto without departing from the scope of the invention as defined in the appended claims.

What we claim is:

1. A method of making a piezo-electric flexible membrane comprising:
    treating a perfluorinated membrane with a hydrogen scavenging compound;
    doping the treated membrane with a cation donating substance; and
    providing an electrical connection to the treated and doped membrane.

2. The method of claim 1 wherein the perfluorinated membrane has the following chemical structure:

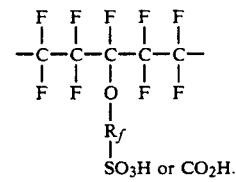

3. The method of claim 1 wherein said treating is performed for about one minute.

4. The method of claim 1 wherein the hydrogen scavenging compound is taken from the group consisting of $NaCO_3$, $CaCO_3$, and $K_2HPO_3$.

5. The method of claim 1 wherein said doping is performed for about 25 minutes.

6. The method of claim 4 wherein the cation donating substance is an organic dye.

7. The method of claim 5 wherein the organic dye is taken from the group consisting of yellow #2 dye, red #40 dye, green dye, and methyl blue #1 dye.

8. The method of claim 1 which is characterized by changing the electrical resistance of the perfluorinated membrane from $\geq 2 \times 10^6$ $\Omega$ to a resistance of $<1 \times 10^9$ $\Omega$.

9. The method of claim 1 wherein the piezo-electric membrane is characterized by a broadside piezo-electric response.

10. A method of making a piezo-electric flexible membrane comprising:
    treating a perfluorinated membrane having an electrical resistance of $\geq 2 \times 10^6$ $\Omega$ to produce a piezo-electric membrane having an electrical resistance of $>1 \times 10^9$ $\Omega$.

11. The method of claim 10 wherein said treating includes treating the perfluorinated membrane with a hydrogen ion scavenging compound and doping the membrane with an organic dye.

12. The method of claim 11 wherein said treating with the hydrogen ion scavenging compound is performed for about one minute and wherein said doping with the organic dye is performed for about 25 minutes.

13. The method of claim 12 wherein the hydrogen scavenging compound is taken from the group consisting of $NaCO_3$, $CaCO_3$, and $K_2HPO_3$ and the organic dye is taken from the group consisting of yellow #2 dye, red #40 dye, green dye, and methyl blue #1 dye.

14. The method of claim 11 wherein the perfluorinated membrane has the following chemical structure:

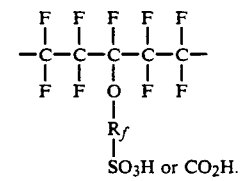

* * * * *